(12) United States Patent
Taylor (10) Patent No.: US 7,732,952 B1
(45) Date of Patent: Jun. 8, 2010

(54) OSCILLATORY MOTORS AND DEVICES INCORPORATING THEM

(75) Inventor: Richard Taylor, Fall City, WA (US)

(73) Assignee: Ultreo, Inc., Seattle, WA (US)

( * ) Notice: Subject to any disclaimer, the term of this patent is extended or adjusted under 35 U.S.C. 154(b) by 53 days.

(21) Appl. No.: 11/777,615

(22) Filed: Jul. 13, 2007

Related U.S. Application Data

(60) Provisional application No. 60/807,460, filed on Jul. 14, 2006.

(51) Int. Cl.
*H02K 33/00* (2006.01)
(52) U.S. Cl. .............................. 310/36; 310/15; 15/22.1
(58) Field of Classification Search ................... 310/36, 310/38, 15, 29, 50; 15/22.1
See application file for complete search history.

(56) References Cited

U.S. PATENT DOCUMENTS

| 4,187,452 | A | | 2/1980 | Knappe et al. |
| 4,334,163 | A | * | 6/1982 | Ascoli ........................... 310/90 |
| 4,543,718 | A | * | 10/1985 | Duescher ...................... 30/124 |
| 4,595,849 | A | | 6/1986 | Cuenoud |
| 5,469,291 | A | * | 11/1995 | Plesko .......................... 359/224 |
| 5,613,259 | A | * | 3/1997 | Craft et al. .................... 15/22.1 |
| 6,833,639 | B2 | * | 12/2004 | Lau et al. ...................... 310/36 |
| 7,116,018 | B2 | * | 10/2006 | Strobl .......................... 310/36 |
| 2004/0183383 | A1 | | 9/2004 | Strobl |
| 2008/0185922 | A1 | * | 8/2008 | Kressner et al. ............... 310/36 |

FOREIGN PATENT DOCUMENTS

WO 2005/043724 A1 5/2005

* cited by examiner

*Primary Examiner*—Michael C Zarroli
(74) *Attorney, Agent, or Firm*—Ann W. Speckman; Speckman Law Group PLLC (57) ABSTRACT

An oscillatory device incorporating a limited angle torque motor capable of oscillating one or more end effector(s) is provided. The device may additionally incorporate an ultrasound transducer and/or a waveguide structure.

16 Claims, 7 Drawing Sheets

OSCILLATORY MOTORS AND DEVICES INCORPORATING THEM

CROSS REFERENCE TO RELATED APPLICATION

This application claims priority to U.S. Patent Application 60/807,460, filed Jul. 14, 2006. The disclosure of the priority application is incorporated by reference herein in its entirety.

BACKGROUND OF THE INVENTION

1. Technical Field of the Invention

The present invention relates generally to the field of oscillatory motors and devices incorporating them, such as portable and hand-held oscillating devices for application as toothbrushes, oral hygiene devices, personal healthcare devices, and the like.

2. Brief Description of Related Art

The use of handheld oscillating devices for personal healthcare and oral hygiene applications such as power toothbrushes, and the like, has increased significantly. Many power toothbrushes employ a motor, generally located in the toothbrush handle, to vibrate or oscillate a brush head and bristle tufts located on a brush head. Other types of personal care and hygiene devices, portable tools, and the like also employ a motor to vibrate or oscillate a component or an accessory. The motors in these devices may be powered, for example, by connection to an electrical power source, by battery power, or by alternative power sources, such as solar or other renewable power sources. Many portable devices utilize rechargeable batteries.

Various types of drive motors may be used to produce oscillation of a component or an accessory or an end effector at "sonic" frequencies below about 1 MHz. A stepper motor may be used to provide oscillating rotary motion of a motor drive shaft that may be coupled to an end effector such as a toothbrush head. Stepper motors are generally controllable to provide precise manipulation of the amplitude of oscillation. Wobble weight motors, conventional rotary motors, gear motors and piezoelectric motors or actuators may alternatively be used as drive motors for producing oscillations at sonic frequencies.

Limited angle torque actuators operate on the principal that a force, or torque, is exerted on a current carrying conductor placed in a magnetic field. The force is proportional to the direction and magnitude of the current and the flux density field. When a permanent magnet flux density field is fixed, the direction of rotation depends on the polarity of the input current, and the amount of torque produced is directly proportional to the magnitude of the input current. Limited angle torque motors typically incorporate a rotor comprising field magnets and a stator supporting armature windings that are wound single phase, unlike conventional brushless motors, which eliminates the need for commutation circuitry. Armature windings may be embedded in slots provided around the inner periphery of a laminated stator or, alternatively, the armature may be toroidally wound on a slotless stator. Limited angle torque actuators are generally used as positioners for operating servovalves, mirrors, antennaes, and other devices that require rotation through relatively small angles.

Motors producing oscillatory motion for use in personal care devices, such as oral hygiene devices and toothbrushes, typically have relatively high mass and inertia drive requirements and typically require higher torque capability than many otherwise suitable motors provide. In addition, the (small) size, (low) weight and (low) noise requirements for motors used in personal care devices are difficult to satisfy. Oscillatory motors of the present invention employing limited angle torque drivers are designed to satisfy these requirements.

SUMMARY OF THE INVENTION

Devices that oscillate a component or an end effector at sonic frequencies of less than 1 MHz and oscillatory motors providing oscillation of components and end effectors at sonic frequencies of less than 1 MHz are provided. The oscillatory motor may be a limited angle torque actuator and generally drives an output shaft through limited angular excursions of less than 180°. The drive output, or angular excursion of an output shaft of the oscillatory motor, may be a limited angular excursion or rotation of an output shaft about its longitudinal axis, or it may be a limited angular excursion of an output shaft in an arc. The oscillatory limited angle torque motor of the present invention preferably incorporates a return mechanism, such as a torsion spring, that returns the output shaft to a neutral position following each angular excursion.

The oscillatory device may be provided as a personal care device or an oral hygiene device such as a power toothbrush, or another device that oscillates a component or an end effector at frequencies of less than 1 MHz. The oscillatory devices may have a unitary construction with the working components integrated in a generally unitary housing, or they may comprise multiple components that are detachable from one another and may be mechanically coupled to provide oscillation to a detachable component or accessory. The oscillatory motors of the present invention may be mounted in a handle component or in an accessory component.

In one embodiment, for example, the oscillatory device comprises a personal care device, such as a power toothbrush or another oral hygiene device having a handle and a detachable accessory, such as a brush head, wherein the oscillatory motor is mounted in the handle and an oscillatory drive shaft extends into a coupled brush head to oscillate the brush head and bristles during operation. When the oscillatory device is a power toothbrush, the detachable accessory may comprise a brush head with bristles and bristle tufts, or the accessory may comprise a probe or flosser attachment, or the like. U.S. Patent Publication Nos. 2005/0091770 A1 and 2007/0079455 A1, which are incorporated herein by reference in their entireties, describe power toothbrushes employing a motor to oscillate bristles in a brush head and make reference to numerous publications relating to power toothbrushes. Oscillatory motors of the present invention are suitable for use in the oral hygiene devices described in these patent publications. More generally, numerous accessories or end effectors may be provided for attachment to a universal handle incorporating an oscillatory motor of the present invention.

Detachable accessories that are oscillated by operation of an oscillatory motor of the present invention may also incorporate features having active or passive power requirements, such as an ultrasound transducer, a motorized device or accessory, light emitting devices, microprocessor controlled circuitry, fluid devices, and the like. Devices of the present invention preferably employ a transformer to inductively couple and transfer power from the power source and/or drive circuitry in one component, such as a handle, to devices having power requirements, such as transducers, light emitting devices, circuitry, and the like, provided in a detachable component or accessory.

The oscillatory device may additionally incorporate a rechargeable power source, such as an inductively rechargeable power source. A charging station connectable to an external power supply for recharging the batteries may also be provided. The battery charging station may include active electronics for charging the batteries from a DC power supply, such as a 12V power supply, in addition to an A/C power supply.

Devices of the present invention may additionally incorporate various user interfaces and control and monitoring features. A user interface comprising at least an on/off control is provided and, upon activation of the device by the user, the oscillatory motor is activated and the oscillatory drive shaft provides oscillatory drive output. A device controller may provide a timing function, various operating cycles may be programmed or programmable, and multiple detachable accessories may be coupled to a universal handle. Multiple detachable accessories may be distinguished by a controller and operated according to predetermined operating cycles. Motor drive oscillatory output may be varied over an operating cycle or according to predetermined or selectable programs. In another embodiment, motor drive oscillatory output may be monitored and varied based on feedback.

BRIEF DESCRIPTION OF THE DRAWINGS

Various aspects and advantages of this invention will become more readily appreciated and may be better understood by reference to the following detailed description, taken in conjunction with the accompanying drawings, wherein.

DETAILED DESCRIPTION OF THE INVENTION

Oral hygiene devices, such as toothbrushes, are exemplary oscillatory devices of the present invention, and detailed embodiments of oscillatory devices are described herein with reference to power toothbrushes. It will be appreciated that devices and features of the present invention are not limited, however, to oral hygiene applications or toothbrushes. The features described herein may be used in various types of personal hygiene and other types of personal care and medical devices, as well as various types of tools. Oscillatory devices of the present invention may comprise a support structure, such as a handle, for housing a limited angle torque motor and having at least one accessory or end effector associated with the support structure that is oscillated at sonic frequencies. The accessory or the end effector may include a bristle, a bristle tuft, a prong, a holder for a detachable implement or material, a razor or skin treatment implement, an implement for treatment of a body structure or tissue, or the like.

Figure 1:
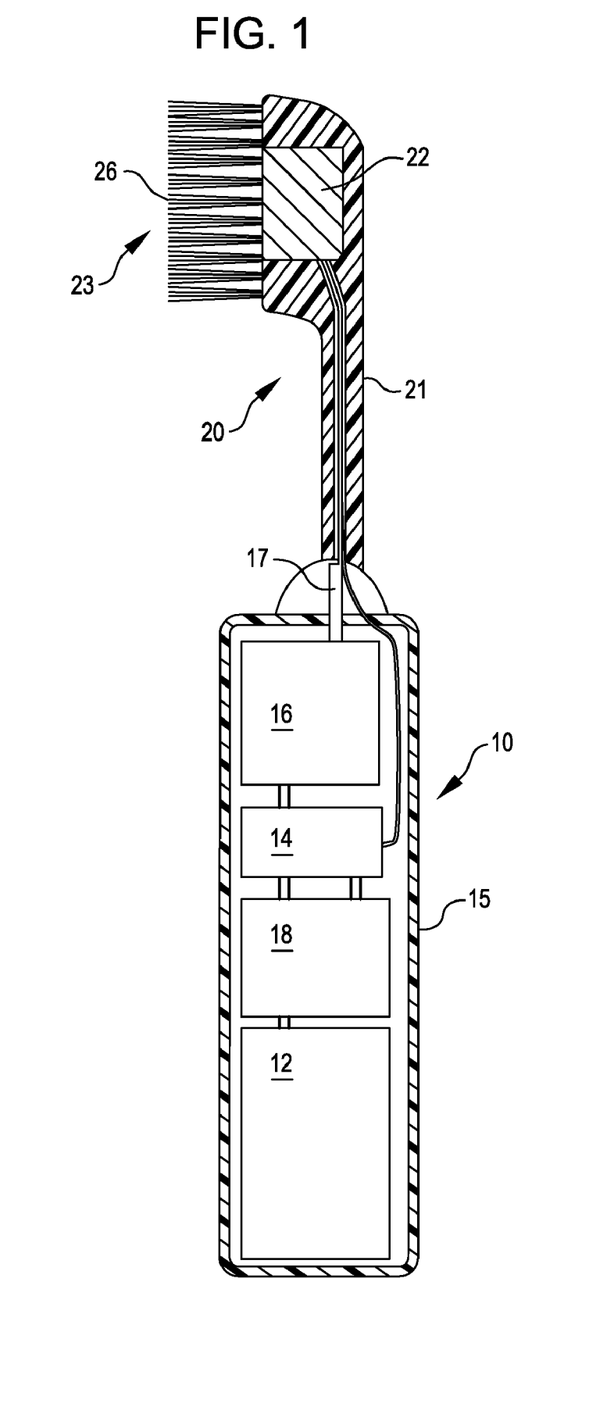
FIG. 1 is a schematic, partially cross sectional diagram depicting an exemplary oral hygiene device of the present invention.

FIG. 1 schematically illustrates an exemplary oral hygiene device of the present invention, a toothbrush, comprising a motor for generating oscillations at sonic frequencies. Toothbrush 10 comprises a handle 15 constructed from a rigid or semirigid material, which typically houses at least one rechargeable battery 12 that may be adapted to be induction charged using a charging device powered by an external power source; a motor 16 for generating oscillation at sonic frequencies, preferably a limited angle torque motor incorporating a return mechanism for oscillating toothbrush head 20 and bristles mounted on the head at sonic frequencies of less than 1 MHz; and controller 18 that provides timing, motor control and various other control functions. The motor may alternatively be mounted in a device accessory that is integral with or attachable to the handle. Toothbrush 10 additionally comprises an electrical drive circuit 14 for driving an active or passive electrical or electronic device. In one embodiment, electrical drive circuit 14 is an ultrasound drive circuit adapted to drive an ultrasound transducer for producing acoustic energy at ultrasonic frequencies at the brush head and motor 16 is mechanically coupled to the brush head by means of an oscillating drive shaft 17 to produce acoustic energy at sonic frequencies at the brush head.

Toothbrush head 20 is mounted on handle 15 and includes a stem portion 21 and brush head portion 23. Stem portion 21 may provide a channel or other means for facilitating transmission of power or instructions to the brush head portion. In the embodiment illustrated schematically in FIG. 1, brush head portion 23 comprises an ultrasound transducer 22 and a plurality of bristle tufts 26. The toothbrush head 20 may be either detachably or fixedly attached to the handle 15 and, in preferred embodiments, is detachably mountable to handle 15. The brush head portion may then be provided as a separate, replaceable component. Ultrasound transducers and modules, acoustic waveguides, and other components facilitating the use of ultrasound transducers in oral hygiene devices are described in detail in U.S. Patent Publication Nos. U.S. 2005/0091770 and U.S. 2007/0079455, which are incorporated herein by reference in their entireties.

The device of FIG. 1 illustrates an exemplary oral hygiene device of the present invention in the form of a power toothbrush. Additional and preferred embodiments including various ultrasound and/or sonic operating parameters, device components, control features, and the like, are described in greater detail in the U.S. Patent Publications incorporated herein by reference. It will be appreciated that while certain combinations of operating parameters and features may be preferred for use in certain applications and in particular environments, the device components, operating parameters, control features, and the like, may be combined in many different ways in oscillatory devices, including oral hygiene devices, of the present invention.

Oscillatory drive motors of the present invention are electrically connected to the power source and may additionally be connected to a controller. They incorporate a drive shaft for delivering motor output, e.g. oscillation, to the device or a device component, or to an accessory such as brush head, to oscillate the brush head and the bristles at sonic frequencies of less than 1 MHz. The motor drive shaft typically projects from the handle assembly and is mechanically coupled to a mating receiving structure in the accessory or the brush head upon mounting of the brush head to the handle. For application in handheld and portable devices, the motor is preferably of a compact and lightweight design that fits conveniently in a generally cylindrical device handle.

Limited angle torque (LAT) devices, which have generally been used as actuators or feedback devices to provide control of angular position, velocity and acceleration, are used in combination with a return mechanism, such as one or more spring(s), as oscillatory drive motors in devices of the present invention. The LAT device provides displacement of an output shaft through an angle of less than 180° and may be configured to provide limited angular displacement as rotation of the output shaft about its own longitudinal axis, or to provide limited angular displacement of the output shaft through an arc, as rotation of the output shaft about an axis generally perpendicular to the longitudinal axis of the shaft. The output shaft is returned to its neutral position following the angular displacement by a centering mechanism, such as a spring. Various types of springs, such as torsion springs, clock springs, leaf springs, clothespin springs, and the like, may be used as return mechanisms in oscillatory drive motors of the present invention. Oscillatory motors of the present invention provide a generally constant torque through the angular displacement and may be designed to provide various ranges of angular displacements.

In one embodiment, LAT motors comprise a magnetic rotor having rare earth permanent magnets that are radially magnetized and a stator that supports windings in a single phase, so that no commutation is required for motion to occur. Because the permanent magnet flux density field is fixed, the direction of rotation depends on the polarity of input current and the amount of torque produced is directly proportional to the magnitude of the input current. In one configuration, described below with reference to the oscillatory drive motor illustrated in FIGS. 2A-2C, the drive motor produces rotation of an output drive shaft through a limited displacement of less than 180° to oscillate the device accessory and/or end effector(s). In another configuration, an oscillatory drive motor of the present invention may be used to produce motion in an arc, or a sweeping side-to-side motion, that is also suitable for use in various types of oral hygiene and other oscillatory devices.

Figure 2A:
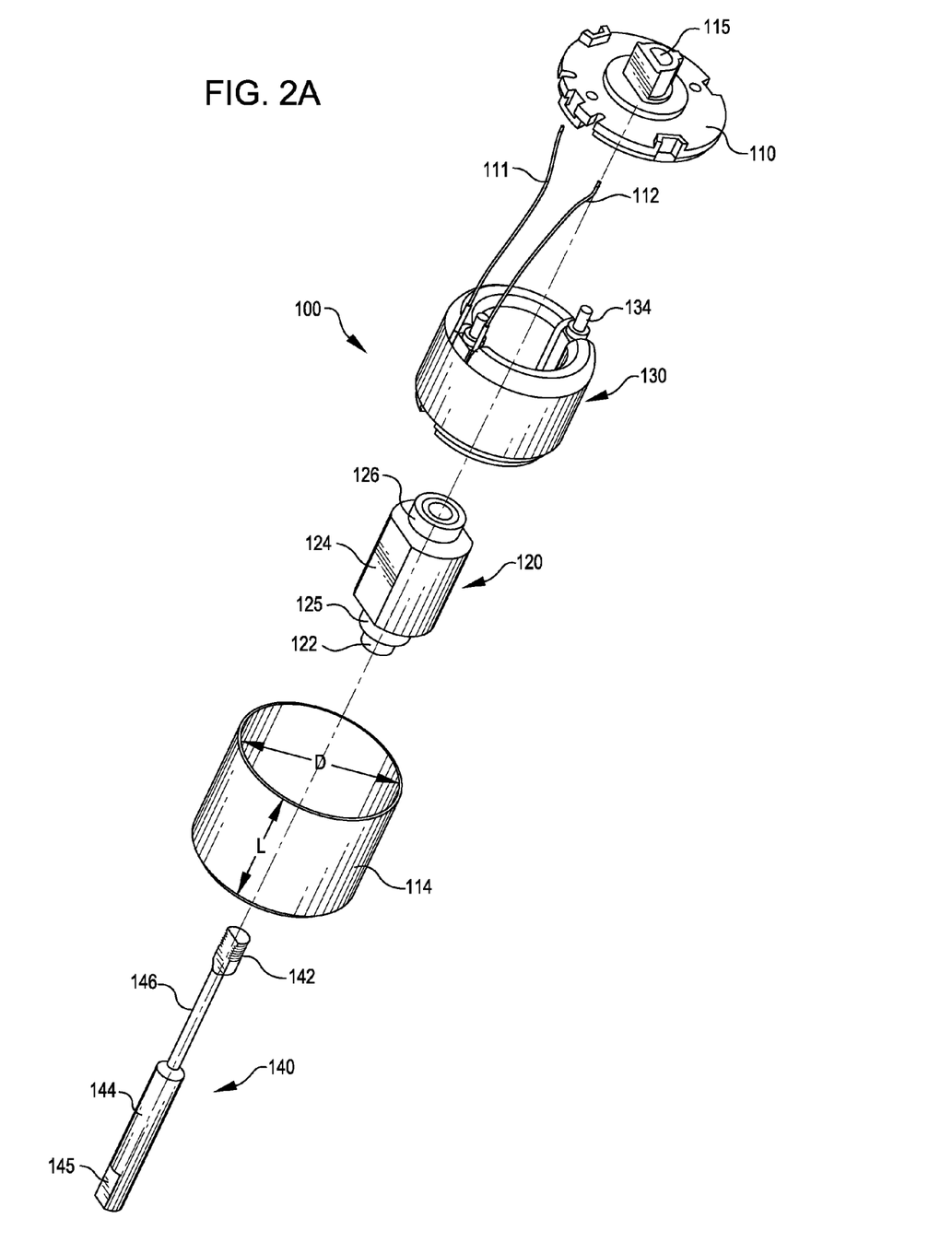
FIG. 2A shows an enlarged schematic exploded perspective view of a limited angle torque motor used in devices of the present invention.
Figure 2B:
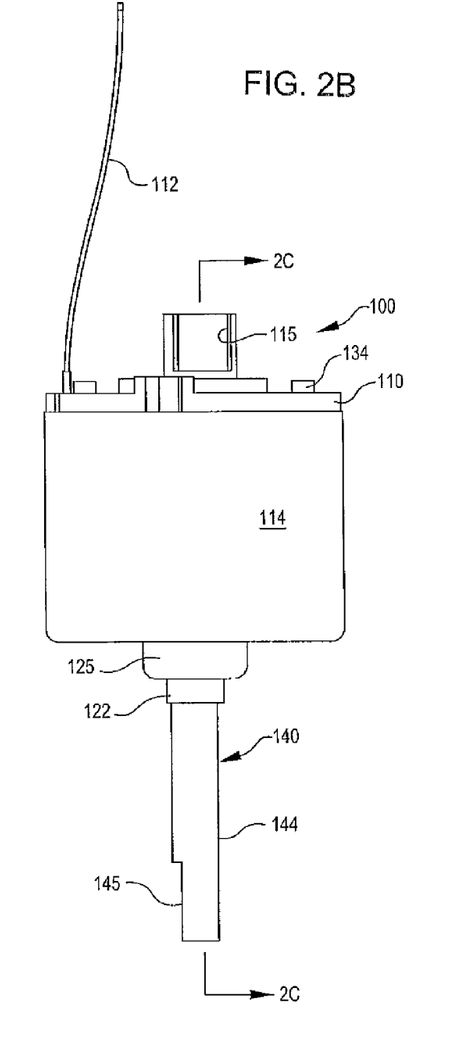
FIG. 2B shows a side view of the limited angle torque motor of FIG. 2A.
Figure 2C:
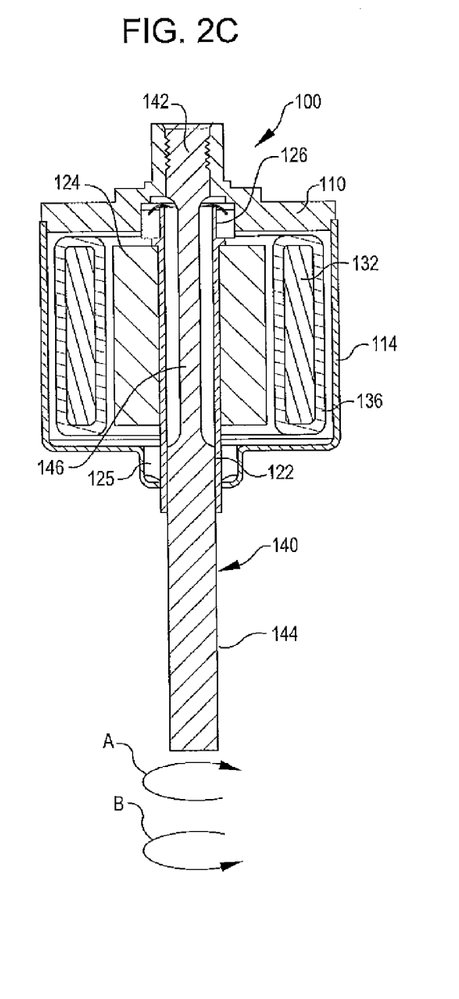
FIG. 2C shows a cross-sectional view of the limited angle torque motor of FIG. 2B taken through line C-C.

FIGS. 2A, 2B and 2C illustrate an oscillatory drive motor producing rotational output suitable for use in oscillatory devices of the present invention. Oscillatory drive motor 100 has a generally cylindrical exterior configuration and comprises a base 110 from which electrical leads 111, 112 that are connected to a stator assembly 130 project. Generally cylindrical housing 114 is mounted to base 110 and encloses rotor assembly 120 and stator assembly 130.

Rotor assembly 120 comprises a central and generally annular core or sleeve 122 on which at least one permanent magnet 124 is retained. Bearings 125, 126 are mounted on sleeve 122 at opposite ends of the magnet. Permanent magnet 124 is preferably a radially magnetized, multipole, rare earth, permanent magnet that is bonded to the sleeve. Multiple Neodymium Iron Boron or Samarium Cobalt permanent magnets may be used for the rotor and arranged to provide an even number of poles (e.g., 2, 4 6, etc.). Drive shaft 140 is fixedly mounted to the rotor assembly by bonding, for example, to the rotor sleeve or core. In a preferred embodiment, drive shaft 140 is bonded to rotor sleeve 122 in proximity to an output portion 144 of the drive shaft.

Stator assembly 130, in this embodiment, is a toroidal coil assembly comprising toroid core 132 having a coil winding 136 mounted on the toroid core. Toroid core 132 preferably comprises an electrically insulated, soft magnetic steel toroid. Multiple sections of coil winding, comprising a magnetic wire material such as insulated copper magnet wire, are wound around the toroid core 132, forming coil 136. The core 132 may have a generally cylindrical configuration or may have an elliptical or another configuration and may comprise a single, unitary core, or split cores may be provided, forming a toroid coil assembly. The coil windings may be bonded or encapsulated, and the number of winding sections of coil 136 corresponds to the number of magnetic poles on rotor assembly 120. Mounting pins 134 or alternative mounting mechanisms are provided on coil assembly 130 for fixedly mounting the coil assembly to the base or to the housing.

In one embodiment useful for compact, oscillatory motors of the present invention, the rotor assembly comprises a single permanent magnet having two opposing poles, and the toroidal coil comprises two coil segments. The longitudinal dimension of the rotor magnet 124 is generally similar to the longitudinal dimension of toroid core 132. Rotor assembly 120 is mounted concentrically within toroidal coil assembly 130 in the embodiment illustrated. Non-concentric arrangements of the rotor assembly within the coil assembly may be used in alternative embodiments and spacers and other types of mechanical devices may be provided to maintain an appropriate distance between the rotor and stator assemblies.

In one embodiment, a motor shaft is mounted, at one portion (e.g., one end), to a stationary structure, such as the motor base or another stationary structure in the device, and is mounted at another portion (e.g. the other end or an intermediate segment) to the rotor assembly. During operation of the motor, the rotor rotates and, with it, a drive portion of the drive shaft is rotated through a limited angular displacement at a desired drive frequency. The direction of rotation depends on the polarity of the input current and, for oscillatory motors of the present invention, the polarity of the input current is generally alternated to provide angular rotational displacement of the output shaft in opposite directions sequentially.

In the oscillatory motor embodiment illustrated in FIGS. 2A-2C, motor shaft 140 is received through the rotor assembly and a stationary end 142 of motor shaft 140 is fixedly mounted in housing base 110. Base 110 may be provided with a keyed bore 115 for receiving a mating, keyed portion of stationary end 142 of motor shaft 140. An opposite end of motor shaft 140 is bonded to the sleeve 122 of the rotor assembly 120. A drive section 144 of the drive shaft extends from motor housing 114 for driving or oscillating a load. A drive portion of drive section 144 may be provided with a flat 145, or another mechanism for mating with a complementary structure in an accessory component, such as a toothbrush head, and orienting the device head with respect to the shaft in both radial and axial orientations.

Oscillatory motors of the present invention preferably incorporate or operate in conjunction with a centering or return mechanism, such as a spring, that re-aligns or returns the poles of the permanent magnet in the rotor assembly to the midpoint of the coil segments of the stator assembly following rotation of the rotor and limited angular displacement of the drive shaft. In one embodiment, the centering mechanism may comprise a torsion spring that returns the shaft to its neutral position following the limited angular displacement. The centering mechanism, in addition to providing the alignment function, allows the rotor assembly to be used as an oscillating resonant system.

In one embodiment, the centering mechanism is provided as a torsion spring forming an integral part of drive shaft 140. As illustrated in FIG. 2A, necked down segment 146 of drive shaft 140 in the area of rotor assembly 120 provides a smaller diameter shaft portion that acts as a centering torsion spring mechanism for the oscillatory motor. In this embodiment, the drive shaft comprises at least one larger configuration segment and at least one smaller configuration segment, with the smaller diameter segment positioned in proximity to the rotor assembly. The drive shaft, as illustrated in FIGS. 2A and 2C, may have two larger diameter segments of unequal dimensions positioned on either side of and formed integrally with the smaller diameter necked down segment 146. The geometry and tensile properties of the smaller diameter segment of the drive shaft forming the torsion spring may be adjusted depending on the angular displacement of the motor, the oscillatory output required, the weight distribution of the driven mass, and the like.

The smaller configuration drive shaft segment that serves as a torsion spring in the embodiment illustrated in FIGS. 2A-2C may have a length of from about 50% to about 200% the length of the rotor magnet, preferably from about 75% to about 150% the length of the rotor magnet. The cross-sectional configuration of drive shaft torsion spring may be cylindrical or may have a flattened profile and may be constant along its length or variable. In one embodiment, for example, the cross-sectional configuration of the drive shaft torsion spring may be tapered. In one embodiment, the cross-sectional configuration of torsion spring 146 generally matches the cross-sectional configuration of the drive section 144 and has a diameter of from about 20% to about 80% the diameter of drive section 144. The torsion spring segment of the drive shaft may be constructed from a material that is the same as that of the rest of the drive shaft, or it may be different and have different tensile properties. In alternative embodiments, the torsion spring may be provided as a flat, pancake-like structure.

The centering mechanism may be integrally formed with the motor shaft within the oscillatory motor housing, as shown in the embodiments illustrated in FIGS. 2A-2C, or it may be provided on an extension of the motor shaft outside the rotor assembly and/or the motor housing. Incorporating the centering mechanism within in the body of the rotor assembly facilitates design of a compact oscillatory motor assembly having a generally low motor housing length to diameter ratio. In some embodiments, the motor housing length (L) to diameter (D) ratio is less than about 1:2 and may be less than about 1:1.5. In some embodiments, the oscillatory motor housing length L is less than less than about 1.5 inch and, in some embodiments, is less than 1 inch.

The geometry and tensile properties of the torsion spring segment of an oscillatory drive shaft, as well as the geometry and properties of the drive segment of the drive shaft, may be adjusted depending on the angular displacement of the motor, the oscillatory output required, the mass of the load being oscillated, and the like. In general, oscillatory motors of the present invention are capable of driving a relatively high mass and inertia accessory, such as a toothbrush head, having a mass and inertia on the order of about $10^{-8}$ $Kg/m^2$ at sonic frequencies of less than about 1 MHz.

Figure 3A:
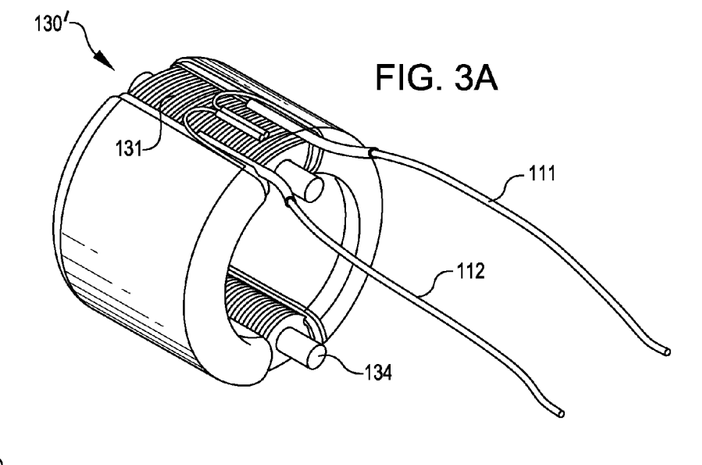
FIG. 3A shows an enlarged schematic perspective view of a limited angle torque motor stator assembly comprising a laminated stack.
Figure 3B:
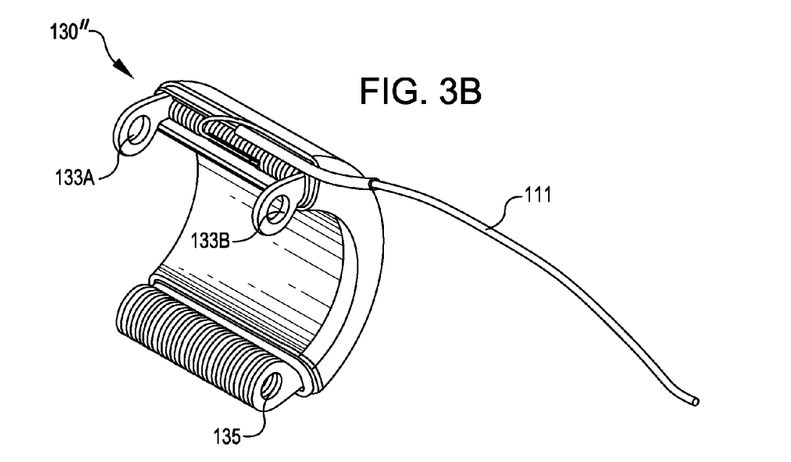
FIG. 3B shows an enlarged schematic perspective view of an exemplary split coil assembly suitable for use in a limited angle torque motor stator assembly.

FIGS. 3A and 3B illustrate alternative stator components and assemblies for use in oscillatory LAT motors of the present invention. The stator assembly illustrated in FIGS. 2A-2C comprises a toroidal coil assembly having a generally solid toroidal core. FIG. 3A shows a stator assembly 130' comprising a toroidal coil assembly having a laminated stack 131 forming the toroidal core. The stator assembly 130' is otherwise similar to that described above with reference to stator assembly 130. The toroidal core may be provided as a unitary, single piece core or, as shown in FIG. 3B, it may comprise two or more separate components assembled to provide a core. FIG. 3B shows a split laminated core section 130" integrating structures for mounting to a mating core section to provide a stator assembly. Split core section 130" comprises eyelets 133A, 133B and a pin receiving structure 135 for mating with complementary structures on another split core section. Insertion of mounting pins through the complementary mating structures provides a unified core for a toroidal coil assembly of the present invention. Two split cores as illustrated in FIG. 3B may be assembled to form a core for a toroidal coil assembly; it will be appreciated that split cores may be provided in various and multiple arced segments.

In operation, when the stationary coil stator assembly is electrically energized, a magnetic field is produced, which causes the permanent magnet in the rotor assembly to rotate with respect to the coil. This rotation of the rotor is mechanically transferred to the segment of the drive shaft mounted to the rotor assembly. Rotation of the rotor assembly thus rotates a portion of the drive shaft in a first direction A, as shown in FIG. 2C, while another portion of the drive shaft is fixedly mounted to a stationary structure, producing the torque output of the motor. In the oscillatory motor assembly of the present invention, as one segment of the drive shaft is rotated with the rotor assembly and another segment of the drive shaft remains in a fixed position with respect to the motor housing, the smaller diameter torsion spring segment 146 of the drive shaft is twisted, or torqued. When the coil is de-energized, the rotor returns to its centered, generally concentric position and the torsion spring returns to its untwisted state. The toroidal coil may then be energized in the opposite direction, shown as direction B in FIG. 2C, rotating the rotor and the drive segment of the drive shaft in the opposite direction, and twisting the torsion spring is in the opposite direction. Again, when the coil is de-energized, the torsion spring returns to its untwisted state and the rotor returns to its centered, concentric position.

This alternating pattern of rotor and drive shaft rotation, and the consequent twisting of the torsion spring in opposite directions, repeatedly rotates a drive segment of the drive shaft along a limited angular rotational path in opposite directions. For many devices and applications described herein, the rotational output of drive portion 144 of drive shaft 140 is less than 20° peak to peak, or less than 10° in both directions from a neutral position. In some embodiments, the angular output of drive portion 144 of drive shaft 140 is less than 10° peak to peak, or 5° in both directions from a neutral position. In yet other embodiments, the angular output of drive portion 144 of drive shaft 140 is between about 2° and 8° peak to peak, or between about 1° and 4° in both directions from a neutral position. For oscillatory oral hygiene devices operating at the frequencies described herein, the angular output of the drive portion 144 of motor shaft 140 is generally from about 2.5° to about 6° peak to peak, and for some applications is between about 3° and 5° peak to peak.

Figure 4:
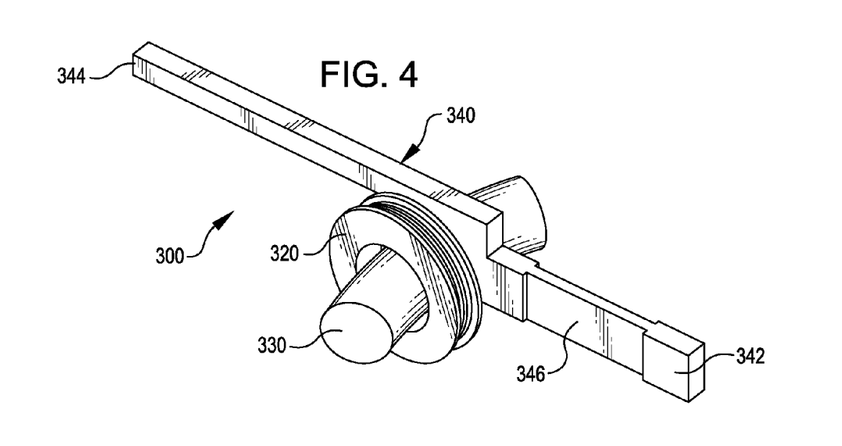
FIG. 4 shows an enlarged schematic perspective view of another embodiment of a limited angle torque motor of the present invention.

Oscillatory motors having a stationary, arced, multiple pole permanent magnet stator assembly and a wound wire rotor may also be used in oscillatory devices of the present invention to provide displacement of an output shaft through an arc rather than as rotation about a shaft. FIG. 4 illustrates an exemplary arc output LAT motor of the present invention. Oscillatory drive motor 300 comprises an arced magnetic stator assembly 330 and a rotor assembly 320. In this embodiment, the rotor assembly has a coil comprising, for example, copper magnet wire, mounted to a portion of an output shaft

340. Another portion of the output shaft, fixed end 342, is mounted to a stationary structure.

When the stator assembly is energized, and the coil rotor moves angularly in one direction along the arc of the magnetic stator and, with it, an output portion 344 of output shaft 340 is displaced through a similar arc. The rotor and output portion of the output shaft are displaced in opposite directions when the polarity of the input current is changed. Oscillatory drive motor 300 preferably comprises a centering mechanism to return the output drive shaft portion 344 to a neutral position. In the embodiment illustrated in FIG. 4, a spring, such as a leaf spring 346, is formed integrally with output shaft 340. In an alternative embodiment, the stationary stator assembly may comprise multipole permanent magnets mounted on plates that are spaced to provide gaps.

The combination of the limited angle torque motor of the present invention incorporating a centering mechanism, and its association with the rotor assembly and the driven mass, such as the accessory device head mechanically coupled to the drive portion of the motor shaft during operation, forms a resonant system. The spring/rotor/driven mass system has a resonant oscillatory frequency that is a function of the moment of inertia of the rotating mass and the spring rate. In preferred devices of the present invention, the moment of inertia of the mass and the spring rate are coordinated so that the resonant frequency of this resonant system is substantially similar to the desired operating frequency of the device accessory (e.g. toothbrush head) and/or end effector(s). Coordinating the resonant frequency of the drive system and the desired device operating frequency is desirable for many applications because it reduces the power consumption of the motor. Alternative embodiments in which the resonant frequency of the spring/rotor/driven mass system and the desired device operating frequency are not matched are also useful for many applications.

The acoustic waveform of sonic oscillations, as generated in devices of the present invention, is generally sinusoidal, but other waveforms may be used—additionally or alternatively. Sonic oscillations may be driven in non-sinusoidal waveforms, for example trapezoidal, triangular, square, purely rotational, and other waveforms. Additionally, the frequency and/or amplitude may be modulated. The frequency of sonic oscillation influences the effectiveness of the device and may additionally influence user comfort and the user's perception of device effectiveness.

For many applications and oscillatory devices of the present invention, the preferred resonant frequency of the spring/rotor/device head system and the preferred oscillating frequency of the driven mass is between about 20 Hz and 10,000 Hz. In a device incorporating one or more end effectors such as bristle tufts or bristles, oscillation of the brush head or accessory at sonic frequencies produces bristle tip motion. Bristle tip motion may be characterized by bristle tip velocity, amplitude, frequency, acceleration, and other metrics. Devices of the present invention employing an oscillatory motor preferably operate to produce bristle tip frequencies of greater than 20 Hz and less than 20,000 Hz. High bristle tip frequencies are irritating to many users and may create an undesirable tickling sensation in the oral cavity. For this reason, bristle tip frequencies of less than about 2,000 Hz are preferred for many oral hygiene device applications. A desired sonic operating frequency may be a note on the musical scale, most typically those have a frequency greater than about 54 Hz and less than about 1662 Hz. According to some embodiments, operation of the oscillatory motor produces bristle tip frequencies of less than about 1500 Hz. Bristle tip frequencies of less than about 1000 Hz are preferred for many applications; bristle tip frequencies of less than about 500 Hz are preferred for yet other embodiments. In still other embodiments, bristle tip frequencies of greater than about 50 Hz and less than about 500 Hz are preferred; in yet other embodiments, the oscillatory motor is operated to produce bristle tip frequencies of between 100 and 300 Hz.

To maintain a generally constant bristle tip velocity as the frequency increases, the bristle tip amplitude decreases. Similarly, to maintain a substantially constant bristle tip velocity as the amplitude increases, the frequency decreases. Both frequency and amplitude of bristle tip movement may affect cleaning and user comfort. Oral hygiene devices of the present invention employing a limited angle torque oscillatory motor, intended for use in the environment of a dentifrice slurry and employing sinusoidal sonic motion, generally operate to produce a desired peak bristle tip velocity during an operating cycle, of from 0 to 10 m/s, more typically from 0.2 to 5 m/s, more typically from 0.4 to 3.0 m/s and generally greater than 1.0 m/sec and less than 3.0 m/s. For some embodiments, the bristle tip velocity during operation is less than about 1.5 m/s, often less than 1.0 m/s, and in some embodiments between about 0.4 and 0.8 m/s. Bristle tip velocity measurements are taken with the bristles dry, in air, without an applied load to the bristle tips. Actual bristle tip velocity is generally reduced during operation as a result of loading associated with frictional contact of the bristles against teeth and drag associated with moving bristles through a fluid environment.

The peak amplitude of bristle tip motion during an operating cycle or subcycle may range from about 0.01 to 10 mm. A preferred range of peak bristle tip amplitude (as wetted and typically loaded in the oral cavity) is in the range of 0.1 to 6 mm, and is generally less than 4.0 mm. According to further embodiments, the peak bristle tip amplitude is less than 3.0 mm and may be in the range of from 0.2 to 3.0 mm or from 0.4 to 2.2 mm. Bristle tip amplitude measurements are taken with the bristles dry, in air, without an applied load to the bristle tips.

Figure 5:
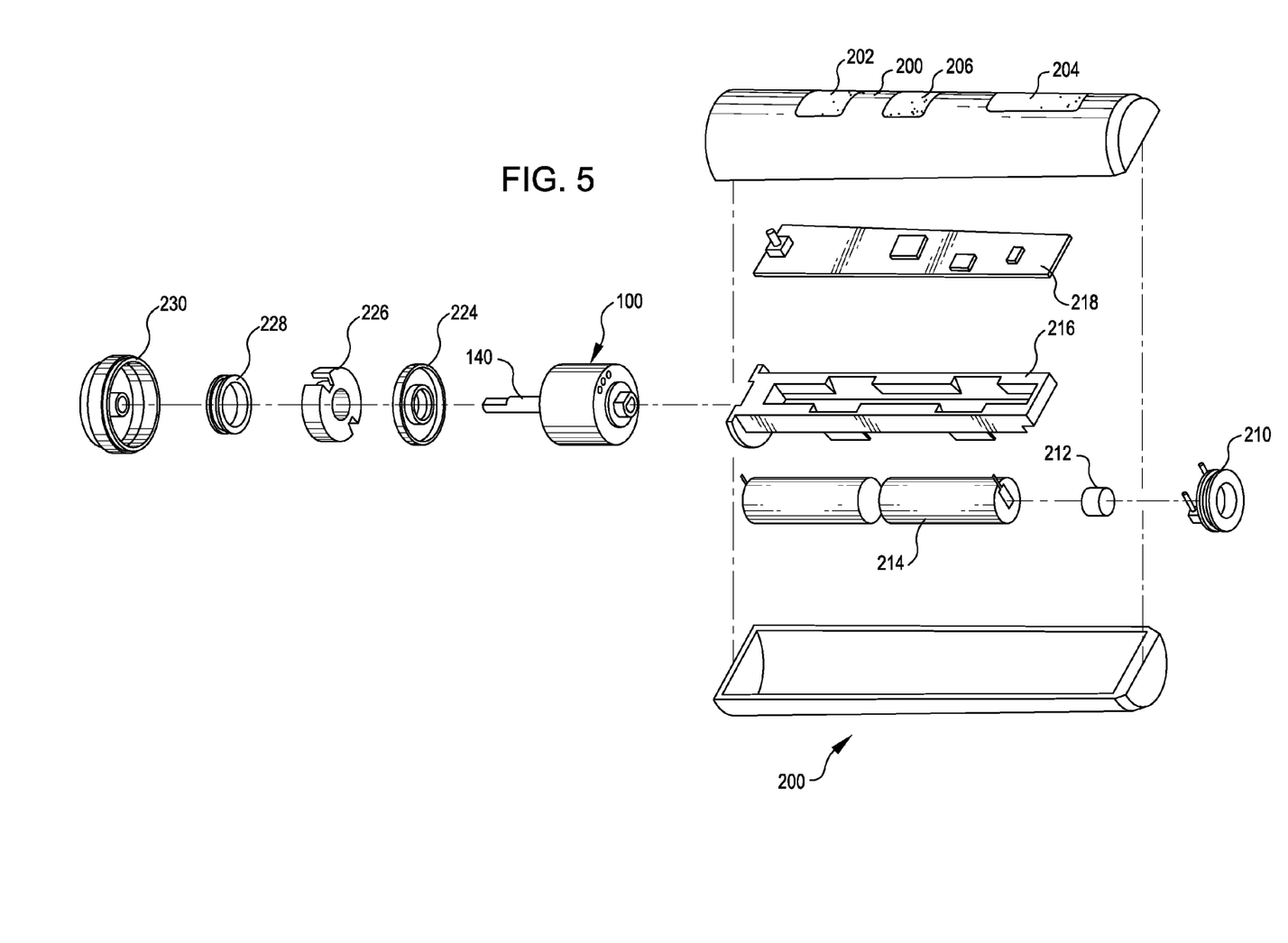
FIG. 5 shows an exploded view of a device handle with a limited angle torque motor and inductive transformer components mounted in a device handle.

An exemplary device handle housing an oscillatory motor of the present invention and other components typically mounted in the handle housing is illustrated in FIG. 5. Handle 200 is generally rigid and has a generally cylindrical profile, with an internal cavity and associated internal mechanical structures for retaining the components shown. The housing may comprise an integral, hollow cylindrical component or it may be formed in one or more pieces, such as an upper and lower part, that are joined during handle assembly. Handle 200 may also incorporate one or more user interface(s), such as on/off button 202, battery charge level indicator 204 and brush head replacement indicator 206.

The motor and other components mounted in the handle that require power may be powered by direct connection to an electrical power source, such as through a conventional cord and plug. Alternatively, the handle may incorporate a battery source for power and may, in preferred embodiments, incorporate a rechargeable battery source. In devices incorporating an inductively rechargeable battery source, a charge coil 210 and charge core 212 are generally provided in the base of the handle assembly for inductive charging from a separate charging station accessing a power supply (See FIG. 7). Charge coil 210 is electrically connected to one or more rechargeable batteries 214 that supply the power requirements for the device. Suitable rechargeable batteries include, for example, Nickel Cadmium (NiCad) batteries and NiMH (Nickel metal hydride) batteries. In the embodiment shown in FIG. 7, batteries 214 are mounted in a mechanical carrier structure 216 that provides mechanical support for the batteries and also supports a controller or circuit board assembly 218. The batteries are preferably located near the center axis of the handle assembly to provide a desirable weight balance to the handle. This housing design allows the shape to be large in the center and taper down at the top and bottom. Different designs of the lower section may be used for different versions of the handle assembly.

In the embodiment illustrated in FIG. 5, a single circuit board assembly 218 is provided and all control and monitoring functions, as well as accessory feature drive circuitry, is provided on the single circuit board. It will be appreciated that these functionalities may be provided on separate circuit boards located in separate locations within the handle, and that additional circuit boards providing additional functionality may also be provided.

Oscillatory devices of the present invention may have a unitary construction or may comprise multiple, detachable components that employ conventional electrical or magnetic contacts to transfer power to components having active or passive power requirements, such as an ultrasound transducer, illumination feature(s), circuitry, and the like, that operate in an accessory component. In one embodiment of an oscillatory device of the present invention, the oscillatory motor is housed in a device handle and one or more components having active or passive power requirements are housed in a detachable accessory component. In this embodiment, inductive coupling of the handle to the accessory component may be provided by a transformer assembly to transfer power from the power source and drive circuitry in the handle to the component(s) in the accessory device head. The transformer assembly may additionally provide a step-up of voltage from power supply circuitry to the powered component and additionally provide a physical separation of the transformer primary and secondary side components when the head assembly is detached from the handle. The transformer assembly also provides electrical isolation between the power supply circuit(s) in the handle and the accessory component circuit in the accessory assembly.

Figure 6:
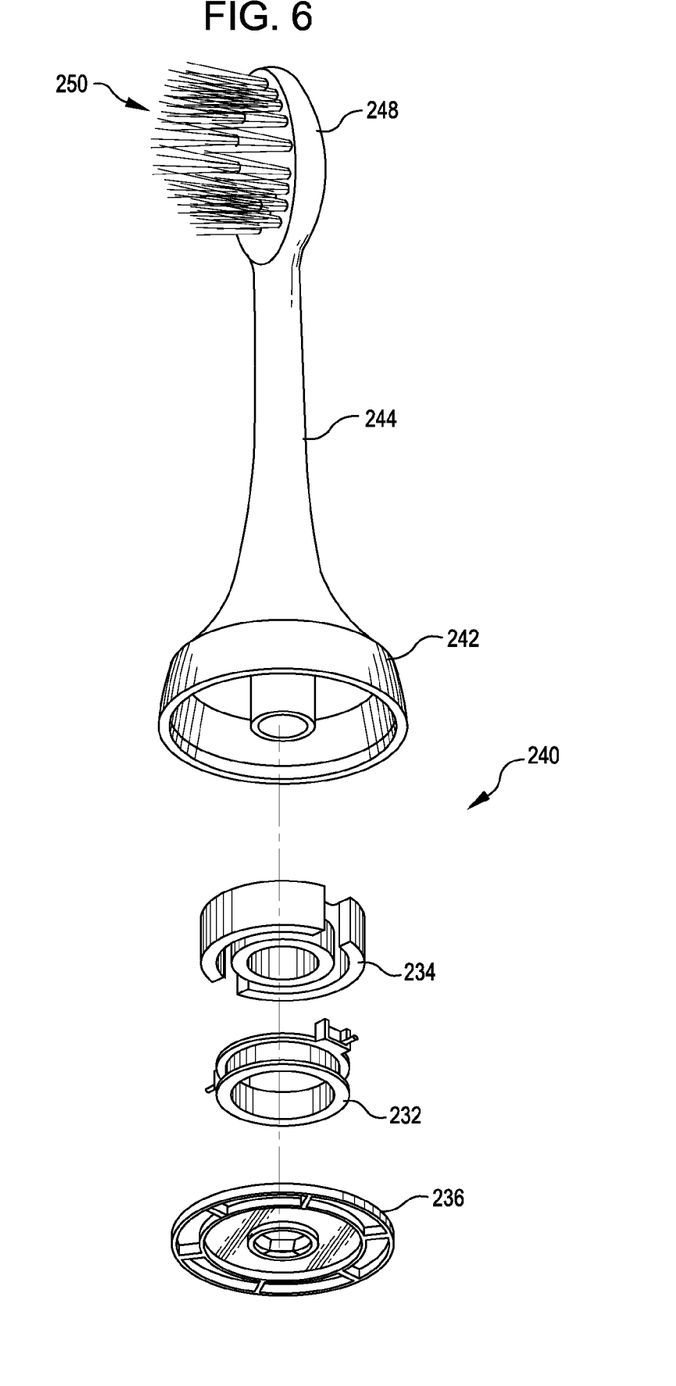
FIG. 6 shows an enlarged exploded view of a device accessory and inductive transformer components mounted in the accessory.

Suitable transformers typically employ a primary and secondary split between the handle and accessory assembly. In one embodiment, a power supply circuit and primary side coil and core of the transformer are mounted in the device handle, and electrical contacts extend from the transformer primary coil into the main handle compartment for connection to a power supply. As illustrated in FIG. 5, the transformer primary coil 228 (electrical contacts not shown) and core 226 components are generally provided in the device handle isolated from the other components mounted in the handle by means of spacer 224 and sealed plug 230. The secondary side coil 232 (electrical contacts not shown) and core 234 of the transformer assembly are mounted in the device head assembly 240 and sealed by cover 236, as illustrated in FIG. 6. The transformer assembly, in this embodiment, delivers an impedance-matched voltage required by the active electrical component provided in the accessory to produce the desired component output. The secondary coil and core, mounted in the accessory, may be mounted in an enlarged housing section 242.

The transformer coil assemblies are typically wound on a bobbin in a circular or elliptical path and sealed. Annular cores having an aperture in the center that permits the oscillatory motor drive shaft to pass through the transformer assembly and mechanically couple to the accessory or another driven mass are preferred for many applications. A small air gap (typically from about 0.010 to 0.150 inch, more typically less than 0.010 inch and, in some embodiments, between 0.040 and 0.080 inch) between the transformer core mounted in the handle and the transformer core mounted in the accessory is desirably maintained during operating cycles for efficient operation of the transformer and inductive power transfer. Within certain embodiments, the air gap between the cores may be achieved by using sealed coil assemblies and having the cores mounted outside these sealed assemblies. In an alternative embodiment, a ferroelectric fluid or ferro-filled elastomer may be used as a filler composition between the cores to improve transformer efficiency.

Alternative transformer designs are also contemplated. These include, without limitation, the use of toroid wound core or lamination stacks to form the core. Regardless of the precise transformer assembly adopted, it may be desirable to have the primary and secondary portions of the transformer split between the handle and toothbrush head assembly.

Within certain embodiments of the present invention, the transformer assembly used for power coupling between the device head assembly and the handle may provide power to other devices requiring power in the device head, and may further provide for the exchange of electrical information between the device head and the handle. This may, for example, be achieved by adding a coil, or an additional coil winding(s), to the primary side of the transformer assembly, or by using a center taped coil, that inductively couples signals to the coil (or coils) in the device head (i.e. the secondary side of the transformer). Thus, a signal may be sent from the handle to the toothbrush head assembly and a corresponding response provided by the toothbrush head assembly components. Alternatively, signals between the primary and secondary sides of the transformer may be coupled to induce a voltage on top of the ultrasonic drive waveform. This may, for example, provide an amplitude modulation signal riding on top of the ultrasound waveform. Alternatively, the signal frequency may be modulated to provide frequency modulation or a combination of frequency modulation and amplitude modulation.

This additional transformer component may, optionally, be employed to provide a feedback signal for monitoring performance of an active electrical component, such as an ultrasound transducer, mounted in the accessory. Such feedback may, for example, control a voltage controlled oscillator (VCO) and/or a phase locked loop (PLL) for self-tuning the oscillator frequency to the transducer, to monitor operation of the ultrasound transducer at the initiation of, or during, an operating cycle or subcycle.

Oscillatory devices of the present invention comprising transformers with one or more extra coil(s), or additional coil winding(s), may incorporate additional device functionality. In one embodiment, for example, the additional coil, or coil winding(s), is primarily used for interaction with an ultrasound transducer power supply circuit. In another embodiment, an additional coil, or coil winding(s), is employed to monitor the performance of an ultrasound transducer. In another embodiment, an additional coil, or coil winding(s), actuates an ultrasound transducer assembly and monitors the performance of the transducer. In yet another embodiment, an additional coil, or coil winding(s), is used for testing and/or calibration of components mounted in the handle and/or device head assembly. In still another embodiment, an additional coil and/or coil winding(s) is used to sense the environment in which the device is used, such as properties in a user's mouth and/or on a user's teeth, and communicate that information to a controller. In another embodiment, an additional coil and/or coil winding(s) is used to determine and/or signal the acceptable or unacceptable performance of an ultrasound transducer or another active electrical component and/or the end of the useful life of an accessory or device head. In yet another embodiment, an extra coil and/or winding(s) may be used to monitor an active component for a unique signature, thereby identifying an accessory and initiating operating cycles based on the sensed accessory.

Accessories oscillated by an oscillatory motor housed in a handle and, optionally, having active components powered inductively by means of a transformer assembly, are preferably detachable from the handle assembly and replaceable. Features of the accessory are illustrated by reference to the toothbrush head assembly illustrated in FIG. 6. Accessory toothbrush head assembly 240 comprises a substantially rigid housing structure, having a base portion 242 for attachment to a mating attachment region on the handle, a smaller cross-section stem portion 244 and a brush head support structure 248. The accessory brush head may incorporate an ultrasound transducer module, and/or one or more bristle tufts 250, as well as the previously described components for transmitting power to the active component and for coupling oscillatory motion to the accessory and bristle tufts. In embodiments that don't incorporate a transformer assembly, electrical power may be provided to the accessory active component by hard-wired electrical connections established by positive contact of complementary electrical contacts mounted in the handle and the accessory upon attachment of the accessory to the handle.

Electrical connection between the secondary coil 232 mounted in the toothbrush head assembly and the active component (e.g., ultrasound transducer assembly) may be accomplished by means of (one or more) conductive electrodes that contact the transducer assembly contact(s) and contacts provided at the secondary coil. One or more conductive electrode(s) may be provided as conductive metal strips retained in channel(s) in the brush head assembly and may be molded into the brush head structure. Alternatively, flexible electrical connections (e.g., jumper-type connections) may be used between the transducer assembly contacts and the coil contacts. In an alternative embodiment, the electrical contacts attach mechanically to the non-moving part of the brush head housing so that the contact provides a spring force to return the brush head to a center position or another desired position.

The bristle tufts 250 are mounted on a support plate or on the support structure 248. Accessory device heads of the present invention, and particularly toothbrush heads, typically incorporate assemblages of one or more bristle tufts, each tuft comprising a bundle of one or more bristle filaments. Many types of bristle filaments are available and may be used in device heads of the present invention. In general, bristle filaments, and tufts, may be characterized by the material of the filaments, the diameter, cross-sectional configuration and exposed length of each filament and tuft, the stiffness or flexibility of filaments and tufts, and the like. The filaments within each tuft may comprise the same material and have the same dimensional properties, or more than one bristle type, shape or size may be incorporated in a single bristle tuft. Likewise, multiple bristle tufts forming the assemblage may comprise the same dimensional and/or physical properties, or bristle tufts having different dimensional properties, lengths, stiffnesses, and the like, may be provided in various arrangements on the brush head. The tufts may comprise bristle filaments of a particular shape and/or size to facilitate both cleaning and user experience. Bristles of a particular shape may be positioned and oriented to complement the presence of a waveguide in the brush head. For example, stiffer bristles and bristle tufts (having a generally greater filament cross section and/or shorter bristle length) may be positioned to facilitate orientation of the waveguide at a particular position with respect to the teeth, and softer bristles (having a generally smaller filament cross-section and/or longer bristle length) may be positioned to facilitate waveguide penetration at interproximal spaces.

Devices of the present invention generally incorporate Power On and Power Off control mechanism(s) that are operable by the user. In one embodiment, a mechanical actuator is provided that, upon application of pressure, activates the device to initiate an operating cycle. Initiation of the operating cycle generally involves activation of the motor drive and/or ultrasound transducer and may incorporate a delay feature that delays initiation of the operating cycle for a predetermined period. The same mechanical actuator may be used to inactivate the device and terminate an operating cycle, or the device may be programmed to automatically shut off after termination of an operating cycle or following a predetermined delay period after termination of an operating cycle. An indication that the device has been activated may be provided by illuminating a Power On button, for example, using LEDs. In addition to Power On and/or Power Off controls, devices of the present invention may have one or more predetermined programmed operating cycles that are selectable by a user. Alternatively, devices of the present invention may be programmable by the user to provide one or more operating cycles selectable by one or more users. Devices of the present invention may additionally incorporate detection features, for example, that allow initiation of an operating cycle only when a device head is appropriately coupled to a device handle, or only when a device head is determined to be operational. In the event a non-functional device head is mounted or a device head is mounted improperly, a user interface may signal the user to make an appropriate correction.

Additional user interfaces may be provided. The level of the battery charge may be enunciated to a user, for example, by illuminating a display visible to the user using LEDs. Variations in the level of charge may be communicated and visualized, for example, by illuminating different quantities or patterns of signals. A user interface may also be provided to indicate that the device head is functioning properly, or that the device head is not functioning. Any type of user interface may be implemented including illumination of an indicator using one or more LED display(s), one or more LCD display(s), an audible tone(s), a pause or change in the operation of the drive motor, or the like. Such indicators may be incorporated variously and in different positions on the device, such as on the handle, on an accessory charging device, on a device head, or on an accessory control device.

A device head, and a device handle, may incorporate an identifier that distinguishes a head or handle from others. Such an identifier may take the form of a color or pattern coded band, light, or other identifying indicia, or may be provided as an electronic identifier detectable upon mounting of the device head in the handle, or by means of an accessory device. Multiple device heads and/or multiple types of device heads may be used with a common handle and may be distinguishable by the user and/or by the controller upon mounting of the device head on the handle. In one embodiment, a device head identifier may be associated with one or more operating protocols such that upon initiation of an operating cycle, the device identifies the device head and runs an operating protocol associated with that device head. Alternatively, if any device head is associated with more than one operating protocol, the device may prompt a user to select a protocol upon or prior to initiation of an operating cycle. The device may similarly detect different types of device heads and initiate appropriate operating cycles depending on the detection and identification of the operating head.

The device controller may provide a timing function that separates a device operating cycle into a plurality of operating subcycles. A plurality of pre-programmed operating periods may be provided, for example, with an audible tone and/or a momentary pause or change in operating conditions producing a user-perceptible division of subcycles. In one embodiment, for example, four generally equal operating subcycles may be provided in a toothbrush of the present invention, providing convenient operation in the four brushing quadrants in the oral cavity. In another embodiment, four generally equal operating subcycles may be provided, followed by a fifth subcycle that is equal or unequal in time to the four previous subcycles. The duration of the operating cycle, for toothbrush applications, may be from about 1 min to 3 min, with operating subcycles generally having a duration of from about 10 sec-45 sec. It will be recognized that any number and combination of subcycles, periods and/or routines may be provided and may be preprogrammed in the device or may be programmable by the user. If multiple preprogrammed subcycle routines are provided, a user interface is provided to allow user selection.

For some oral hygiene applications, the oscillatory motion (bristle tip velocity, amplitude and/or frequency) is desirably greater during some periods of an operating cycle and/or an operating subcycle than at others. In some embodiments, therefore, the motor drive output producing oscillatory motion is variable over an operating cycle of the device. In another embodiment, devices of the present invention employing a drive motor are capable of determining and controlling the desired motor drive operating frequency by monitoring the resonant operating conditions of the motor. The controller may, for example, monitor both the current drawn by the drive motor and the drive frequency of the motor on a continuous or intermittent basis. The resonant frequency of the motor is detectable by monitoring the current, since the current required is lower when the motor operates at its resonant frequency. The controller may then set the drive motor operating frequency to a desired offset from the determined resonant frequency, or vary the drive motor operating frequency to achieve a desired resonant frequency under different operating conditions.

Alternatively, the motor operation may be monitored on a continuous or intermittent basis and the electromotive force (EMF) detected from the motor may be used to determine the natural resonant frequency of the motor and/or its driven system, including the brush head. Since the resonant frequency is different with and without the brush head installed, this system may be used to determine if a brush head is attached to the handle. Multiple brush heads having different inertia properties may also be detected and identified using this system, thereby identifying different users and, optionally, matching different protocols or programmed features to the different users and/or brush heads. This system may also be used in conjunction with a brush head replacement feature, to detect and identify replacement brush heads and thereby trigger a reset operation.

An accessory device may also be used, in conjunction with the controller monitoring the drive motor frequency, to monitor the angular amplitude for each frequency. The resonant frequency of the motor is detectable by monitoring the angular amplitude for each frequency. The angular amplitude measurements may be communicated to the controller, which then sets the drive motor operating frequency based on the determined resonant frequency, as above.

Figure 7:
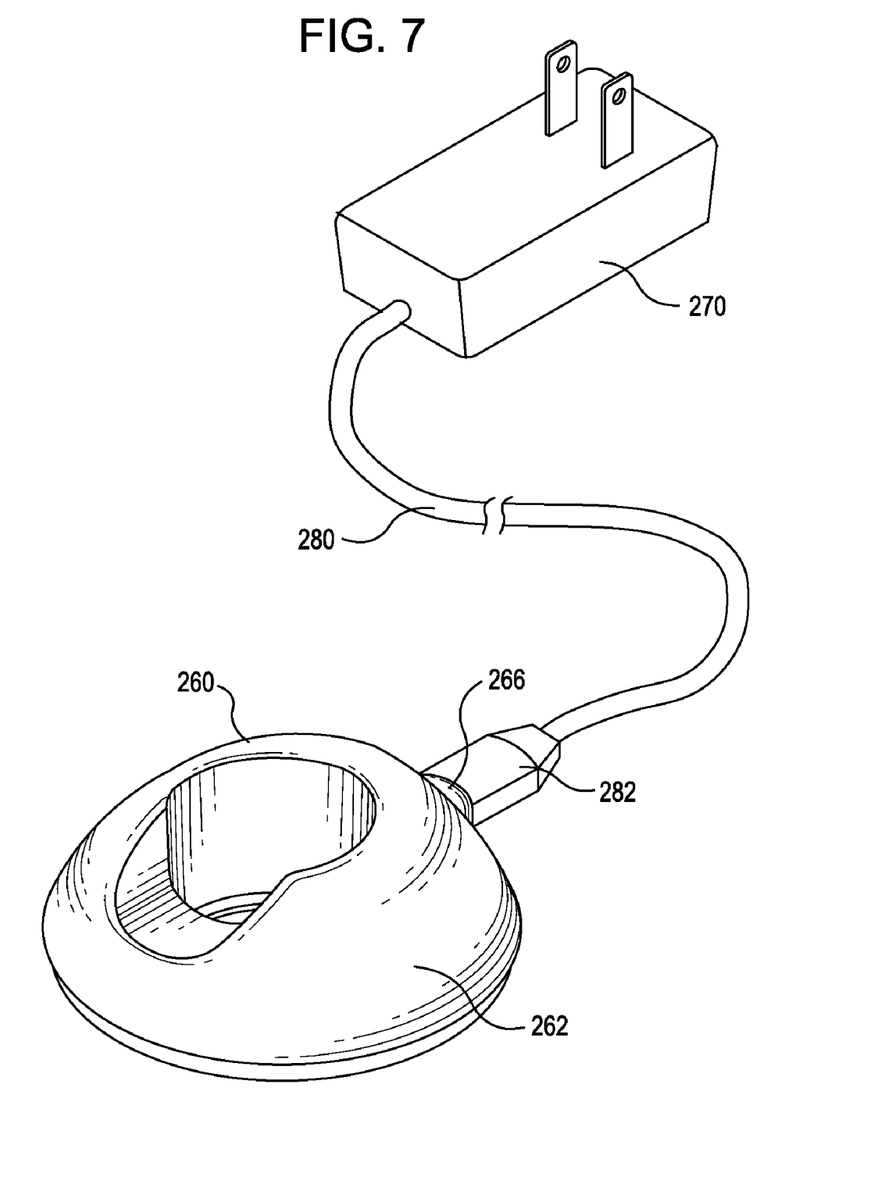
FIG. 7 shows a schematic view of a charging station and power cord useful in connection with devices of the present invention.

The oscillatory device of the present invention may incorporate batteries that are rechargeable using an inductive charging assembly as illustrated in FIG. 7. FIG. 7 illustrates a charger assembly including an inductive charger base 260 incorporates recess 262 and an open access area that facilitates placement of a mating device handle in the charger base. Base 260 is preferably constructed from a rigid, non-conductive material, such as a rigid plastic, and may be provided with one or more non-skid stabilizers on its bottom surface. Base 260 has an internal space enclosing an inductive coupling coil and core for inductive charging of the batteries through the complementary charge coil/core combination in the handle.

Base 260 is electrically connectable to an electrical source through plug 270 by means of flexible cord 280. Plug 270 may have prongs and be configured to connect to an alternating current source, such as a standard electrical outlet, or may be configured to connect to a direct current source. Cord 280 has a plug 282 that mates with receptacle 266 in charger base 260 and is electrically connected to plug 270 at its opposite end. A single prong or multiple prong plug/receptacle combination may be provided. In one embodiment, cord 270 is detachably connectable to charger base 260 by means of the detachable connection of plug 282 to receptacle 266 to permit more convenient storage and charging of the device. In one embodiment, charger base 260 comprises active charging elements that permit inductive charging of rechargeable batteries in the handle from multiple electrical sources, such as from an alternating current (AC) source, or from a direct current (DC) source.

All references to ranges of parameters described in this specification are understood to include reference to a range equal to and greater than the lower value of each range, as well as ranges equal to and less than the higher value of each range. Thus, for example, the recitation of a carrier frequency of between about 250 and about 500 kHz in this specification is interpreted to include carrier frequencies of 250 kHz and greater; carrier frequencies of 500 kHz and less; as well as carrier frequencies within the stated range.

It will be appreciated that while the use of an oscillatory limited angle torque motor to oscillate a device or a device accessory or end effector at sonic frequencies has been described with reference to a power toothbrush, this arrangement may be used in other types of oral hygiene devices and, indeed, in other types of personal care and medical devices, as well as tools. The combination of the oscillatory motor of the present invention with a transformer assembly for providing power to active components in a detachable accessory likewise has application for many types of oscillatory devices.

I claim:

1. An oscillatory motor comprising a rotor assembly, a drive shaft mounted to move with the rotor assembly, a stator assembly, and a centering mechanism, wherein the rotor assembly incorporates at least one permanent magnet having an even number of poles, the stator assembly incorporates a toroidal coil assembly having at least one toroid core with a coil winding mounted outside and concentrically with the magnetic rotor, whereby when the toroidal coil assembly is energized, the rotor assembly and drive shaft are rotated with respect to the toroidal coil assembly from a neutral position through an arc or an angular displacement of less than 180° and the drive shaft is returned to a neutral position by the centering mechanism, and wherein the rotor assembly and drive shaft are rotated in opposite directions from the neutral position with respect to the toroidal coil assembly when the polarity of the input current is changed.

2. An oscillatory motor of claim 1, wherein the rotor assembly comprises a single permanent magnet having two opposing poles and the stator assembly comprises at least two core sections assembled to provide a toroidal core.

3. An oscillatory motor of claim 1, wherein at least one drive shaft segment is mounted in a stationary structure and remains stationary during rotation of the rotor assembly.

4. An oscillatory motor of claim 1, wherein the centering mechanism is a spring.

5. An oscillatory motor of claim 4, wherein the centering mechanism is a torsion spring.

6. An oscillatory motor of claim 5, wherein the torsion spring is formed integrally with the drive shaft as a smaller diameter drive shaft section.

7. An oscillatory motor of claim 4, wherein the centering mechanism is mounted inside the magnetic rotor.

8. An oscillatory motor of claim 1, wherein the angular output of a drive portion of the drive shaft is less than 10° in each direction from the neutral position.

9. An oscillatory device comprising: a handle housing a power supply and an oscillatory motor having a rotor assembly, a drive shaft mounted to move with the rotor assembly, a stator assembly, and a centering mechanism, wherein the rotor assembly incorporates at least one permanent magnet having an even number of poles, the stator assembly is mounted outside and concentrically with the magnetic rotor and incorporates a toroidal coil assembly having at least one toroid core with a coil winding, whereby when the stator assembly is energized, the rotor assembly and drive shaft move from a neutral position through an arc or an angular displacement and, when the stator assembly isn't energized, the drive shaft is returned to the neutral position by the centering mechanism, and the rotor assembly and drive shaft are rotated in opposite directions from the neutral position with respect to the toroidal coil assembly when the polarity of the input current is changed; and an accessory that is adapted to be mechanically coupled to the drive shaft; wherein the combination of the oscillatory motor and the accessory form a resonant system.

10. An oscillatory device of claim 9, wherein the resonant frequency of the resonant system is between 20 Hz and 10,000 Hz.

11. An oscillatory device of claim 9, wherein resonant frequency of the resonant system is greater than about 50 Hz and less than about 500 Hz.

12. An oscillatory device of claim 9, wherein the power supply is a rechargeable battery mounted in the handle.

13. An oscillatory device of claim 12, wherein the rechargeable battery is inductively chargeable, and a charge coil and a charge core are additionally mounted in the handle.

14. An oscillatory device of claim 13, additionally comprising a charger assembly including an inductive charger base for inductive charging of the rechargeable battery, a cord detachably connectable to the charger base at one end and connectable to an electrical source by means of a plug at the other end.

15. An oscillatory device of claim 14, wherein the charger base incorporates charging elements that permit inductive charging of rechargeable batteries from multiple sources, including alternating current sources and direct current sources.

16. An oscillatory device of claim 9, wherein the accessory is detachable from the handle.

\* \* \* \* \*